(12) United States Patent
Kawanishi et al.

(10) Patent No.: US 6,188,925 B1
(45) Date of Patent: Feb. 13, 2001

(54) BODY FAT DETERMINING DEVICE

(75) Inventors: Shozo Kawanishi, Nishinomiya; Masami Yamanaka, Miki; Yasutoshi Masuda, Akashi, all of (JP)

(73) Assignee: Yamato Scale Co. Ltd.,, Akashi (JP)

( * ) Notice: Under 35 U.S.C. 154(b), the term of this patent shall be extended for 0 days.

(21) Appl. No.: 09/164,287

(22) Filed: Oct. 1, 1998

(30) Foreign Application Priority Data

Dec. 25, 1997 (JP) .................................................. 9-357510

(51) Int. Cl.$^7$ .................................................. A61B 5/05
(52) U.S. Cl. ........................... 600/547; 345/173; 345/174
(58) Field of Search .................................... 600/547, 546, 600/548; 128/734, 659; 345/173, 174

(56) References Cited

U.S. PATENT DOCUMENTS

| | | | |
|---|---|---|---|
| 4,947,862 | * 8/1990 | Kelly ..................... | 128/734 |
| 4,949,727 | * 8/1990 | Yamazaki et al. ........ | 128/734 |
| 5,335,667 | * 8/1994 | Cha et al. ............... | 128/734 |
| 5,372,141 | * 12/1994 | Gallup et al. ............ | 128/734 |
| 5,415,176 | * 5/1995 | Sato et al. .............. | 128/734 |
| 5,579,782 | * 12/1996 | Masuo .................... | 128/734 |
| 5,611,351 | * 3/1997 | Sato et al. .............. | 128/734 |
| 5,817,031 | * 10/1998 | Masuo et al. ............ | 600/547 |

FOREIGN PATENT DOCUMENTS

| | | |
|---|---|---|
| 5-2164 | 5/1987 | (JP) . |
| 1-119614 | 8/1989 | (JP) . |

* cited by examiner

Primary Examiner—Marvin M. Lateef
Assistant Examiner—Jeoyuh Lin
(74) Attorney, Agent, or Firm—Marshall, O'Toole, Gerstein, Murray & Borun

(57) ABSTRACT

Provided is a small-sized body fat determining device capable of easily determining a body fat ratio. A first electrode pair (1) and a second electrode pair (2) are provided on upper left and right sides of a surface (11a) and a back face (11b) of a card body (11) of a card type electronic calculator, respectively. The first electrode pair (1) includes a first measuring electrode (1a) provided on the surface (11a) of the card body (11), and a first current path forming electrode (1b) provided on the back face (11b) of the card body (11). The second electrode pair (2) includes a second measuring electrode (2a) provided on the surface (11a) of the card body (11), and a second current path forming electrode (2b) provided on the back face (11b) of the card body (11). An impedance between the first measuring electrode (1a) and the second measuring electrode (2a) is measured by impedance measuring means provided in the card body (11).

9 Claims, 3 Drawing Sheets

BODY FAT DETERMINING DEVICE

FIELD OF THE INVENTION

The present invention relates to a body fat determining device, and more particularly to a body fat determining device capable of easily determining a body fat ratio by causing a subject's fingertips to come in contact with an electrodes of the body fat determining device held in hands.

DESCRIPTION OF THE RELATED ART

Conventionally, attention has been given to a body fat ratio in respect of maintenance of health. If the body fat ratio is increased, adult diseases and the like are caused. Therefore, measurement of the body fat ratio is available to prevent the adult diseases. There has been known a body fat ratio determining device wherein two electrodes forming a current path and voltage measuring electrodes for measuring an impedance between two points on the current path are provided on a scale. These electrodes are positioned on a base of a scale where feet of the subject are put. By using such a body fat ratio determining device, it is possible to simultaneously measure data on a weight which is necessary when a body fat ratio is to be obtained. Therefore, the body fat ratio determining device is convenient.

There has also been developed a device for determining a body fat ratio by holding a handle in both hands. The body fat determining device has an advantage that a body fat ratio can be measured comparatively easily unlike the above-mentioned device provided to the scale.

Furthermore, Japanese Utility Model Publication No. Hei 5-2164 has disclosed a body fat determining device comprising two sets of electrode pairs, each electrode pair having a current path forming electrode and a voltage measuring electrode provided very closely on a surface of a card. In the body fat determining device, one finger of one hand is caused to come in contact with both the current path forming electrode and the voltage measuring electrode of one of the electrode pairs and one finger of the other hand is caused to come in contact with both the current path forming electrode and the voltage measuring electrode of the other electrode pair. The card type body fat determining device has an advantage that a body fat ratio can readily be measured.

The conventional body fat determining device provided to the scale as described above is suitably placed in a bathroom and the like. However, it is necessary to determine the body fat ratio at least with socks taken off. Therefore, the body fat ratio cannot easily be measured. Furthermore, feet are not always placed on a constant position when a subject gets on the base. A distance between impedance measuring points on the current path is varied every measurement so that different results of the measurement are obtained.

On the other hand, the handle type body fat determining device has no trouble that socks should be taken off. Therefore, the body fat ratio can be measured comparatively easily. In the handle type body fat determining device, however, the distance between the impedance measuring points on the current path is varied every measurement depending on a manner of grasping the handle. Consequently, different results of the measurement are obtained. The body fat determining device of this type cannot be carried. Therefore, the body fat ratio cannot easily be measured. Accordingly, the body fat determining device can be used by only purchasers' family.

In the above card type body fat determining device, furthermore, one of fingers should be caused to come in contact with the current path forming electrode and the voltage measuring electrode which form one electrode pair. Accordingly, it is necessary to reduce an electrode area. Consequently, inaccurate results of measurement are inevitably obtained. In addition, the current path forming electrode and the voltage measuring electrode which form one electrode pair should be provided very closely. For this reason, a leakage current is increased between the electrodes so that the results of the measurement become more inaccurate.

SUMMARY OF THE INVENTION

In order to solve the above-mentioned problems of the body fat determining device according to the prior art, it is an object of the present invention to provide a small-sized body fat determining device capable of determining a body fat ratio easily and comparatively accurately without varying a distance between impedance measuring points on a current path every measurement.

The body fat determining device according to the present invention serves to determine a body fat ratio by using fingers of both hands. More specifically, a current path is formed through a human body between fingers of each of hands and an impedance between two points of fingers of each of hands other than the above-mentioned fingers forming the current path is measured. Thus, the body fat determining device has a structure in which measurement can be performed by the fingers of the hands. Consequently, the body fat determining device can be handy and easy to carry. Furthermore, because the formed current path has a constant length, a variation in a value of the impedance obtained for each measurement is reduced. In addition, a body fat ratio can accurately be measured by a simple operation in which fingers of both hands are caused to come in contact with electrodes.

DESCRIPTION OF THE PREFERRED EMBODIMENTS

Figure 1:
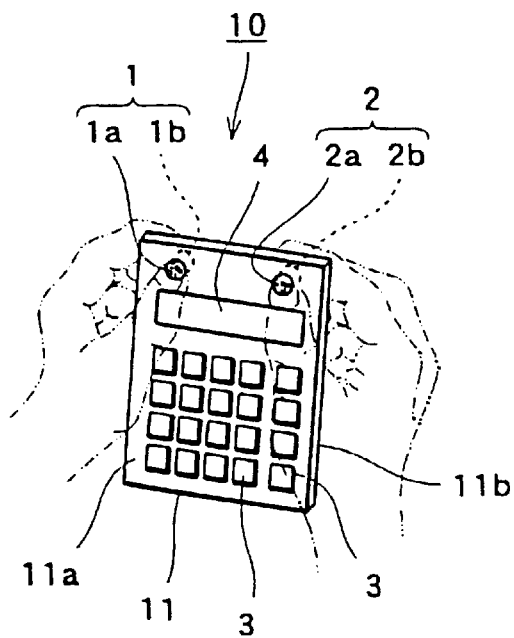
FIG. 1 is a perspective view showing a body fat determining device according to an embodiment of the present invention.

An embodiment of the present invention will be described below. A body fat determining device according to the present invention comprises two electrode pairs, each electrode pair including a current path forming electrode and a measuring electrode. More specifically, a first electrode pair has a first current path forming electrode and a first measuring electrode, and a second electrode pair has a second current path forming electrode and a second measuring electrode. A current is caused to flow between the first current path forming electrode of the first electrode pair and the second current path forming electrode of the second electrode pair. A current path is formed between these electrodes in a human body. The first measuring electrode of the first electrode pair and the second measuring electrode of the second electrode pair are provided in order to measure an impedance between two points in the middle of the current path formed in the human body. Thus, these four electrodes are provided in order to form the current path between two current path forming electrodes and to measure the impedance between the two points in the middle of the current path, thereby eliminating an influence of the impedance on a contact portion of the electrodes with a skin of the human body.

In the body fat determining device according to the preset invention, the first and second current path forming electrodes and the first and second measuring electrodes are provided respectively in positions where one finger of each of the subject's hands can electrically contact with each of the first and second measuring electrodes and other fingers of the subject's hands can electrically contact with each of the first and second current path forming electrodes. Since these electrodes are provided in such positions, a current path is formed between the other fingers of each of the subject's hands through each arm and a body. An impedance of the human body is measured on two points in the middle of the current path, that is, on the current path between said one of the fingers of each hand through each arm and the body. The impedance is measured by impedance measuring means. In the body fat determining device according to the present invention, fingertips are caused to come in contact with the current path forming electrodes and the measuring electrodes. Consequently, positions where the fingertips contacts with the electrodes are almost constant for each measurement. Accordingly, the formed current path has a constant length. As a result, a variation in a value of the impedance obtained for each measurement is reduced.

Data on the subject which are necessary for calculation of a body fat ratio, for example, a weight, a height, an age, a sex and the like are input from data input means. Furthermore, the body fat ratio is calculated by calculating means based on the impedance obtained by the impedance measuring means and the data on the subject which are input from the data input means.

One aspect of the present invention is directed to a body fat determining device in which one of the fingers is a thumb and the other fingers are fingers except the thumb. According to this aspect of the present invention, the first and second current path forming electrodes and the first and second measuring electrodes are provided in positions where the thumb of each of subject's hands can electrically contact with each of the first and second measuring electrodes and fingers other than the thumb of each of the subject's hands can electrically contact with each of the first and second current path forming electrodes. These electrodes are provided in such positions so that a current path is formed between the fingers other than the thumb of each of the subject's hands through each arm and a body. An impedance is measured on two points in the middle of the current path, that is, on the current path between the thumbs of each hand through each arm and the body.

Other aspect of the present invention is directed to the body fat determining device, wherein the body fat determining device is of a card type, the first current path forming electrode and the second current path forming electrode are provided on one of faces of the card type body fat determining device, and the first measuring electrode and the second measuring electrode are provided on the other face of the card type body fat determining device. The first measuring electrode is provided in a position just behind the first current path forming electrode. Similarly, the second measuring electrode is provided in a position just behind the second current path forming electrode. With such a structure, it is easy to determine a body fat ratio by a simple operation for holding the card type body fat determining device in both hands. In addition, each measuring electrode is provided in a position just behind each corresponding current path forming electrode. Therefore, the finger can surely be caused to electrically contact with each electrode.

Further aspect of the present invention is directed to the body fat determining device, wherein the body fat determining device is of a card type, the first current path forming electrode and the second current path forming electrode are provided on one of end faces of the card type body fat determining device, and the first measuring electrode and the second measuring electrode are provided on the other end face of the card type body fat determining device. The first measuring electrode, the first current path forming electrode, the second measuring electrode and the second current path forming electrode are provided in such a manner that the thumbs of both hands are positioned on the first and second measuring electrodes and the fingers other than the thumbs of the hands are positioned on the first and second current path forming electrodes when the card type body fat determining device is held in the hands. Also in such a structure, it is easy to determine a body fat ratio by a simple operation for holding the card type body fat determining device in both hands. In addition, the finger can surely be caused to electrically come in contact with each electrode.

Further aspect of the present invention is directed to the body fat determining device, wherein the body fat determining device is of a card type, the first current path forming electrode and the first measuring electrode are provided on one of faces of the card type body fat determining device, and the second current path forming electrode and the second measuring electrode are provided on the other face of the card type body fat determining device. According to this aspect of the present invention, it is easy to determine a body fat ratio by supporting the card type body fat determining device on both faces between fingers of both hands.

Further aspect of the present invention is directed to the body fat determining device, wherein the body fat determining device is of a card type, and the first and second current path forming electrodes and the first and second measuring electrodes are provided on one of faces of the card type body fat determining device. According to this aspect of the present invention, the card type body fat determining device is put on a table or the like with these electrodes placed on an upper face, two fingers of one of hands are caused to come in contact with the first current path forming electrode and the first measuring electrode respectively, and two fingers of the other hand are caused to come in contact with the second current path forming electrode and the second measuring electrode respectively. Consequently, a body fat ratio can easily be measured.

Embodiment

FIG. 1 is a perspective view showing a body fat determining device according to an embodiment of the present invention. The body fat determining device according to the present embodiment is of a card type, and has a function of determining a body fat ratio added to a card type electronic calculator. As shown in FIG. 1, a body fat determining device 10 according to the present embodiment has a first electrode pair 1 provided on a surface 11a and a back face 11b on the upper left side of a card body 11, and a second electrode pair 2 provided on the surface 11a and the back face 11b on the upper right side of the card body 11. The first electrode pair 1 includes a first measuring electrode 1a provided on the surface 11a of the card body 11, and a first current path forming electrode 1b provided on the back face 11b of the card body 11. The first current path forming electrode 1b is provided on just a back of the first measuring electrode 1a. Similarly, the second electrode pair 2 includes a second measuring electrode 2a provided on the surface 11a of the card body 11, and a second current path forming electrode 2b provided on the back face 11b of the card body 11. The second current path forming electrode 2b is provided on just a back of the second measuring electrode 2a. An impedance between the first measuring electrode 1a and the second measuring electrode 2a is measured by impedance measuring means (not shown) which is provided in the card body 11. The impedance measuring means can be implemented by a known impedance measuring apparatus.

The body fat determining device 10 according to the present embodiment has a number of keys 3. The keys 3 realize the function of the electronic calculator and also function as data input means for inputting data on a subject's weight, height, age, sex and the like. The card body 11 is provided with calculating means for calculating a body fat ratio based on the impedance obtained by the impedance measuring means and the data on the subject which are input by means of the keys 3. The calculating means can be implemented by a CPU and a memory which realize the function of the electronic calculator. In the present embodiment, a display section 4 is provided to confirm input numeric values and to display the body fat ratio which is finally obtained. The display section 4 is also used to indicate an operation value for utilization as the electronic calculator and a result of the calculation.

The body fat ratio can be measured using the body fat determining device 10 according to the present embodiment, as shown in a two-dotted chain line of FIG. 1, by causing the subject to hold the body fat determining device 10 with thumbs and index fingers of both hands, for example. More specifically, the body fat determining device 10 is held in such a manner that the thumb of a left hand presses the first measuring electrode 1a and the index finger of the left hand presses the first current path forming electrode 1b. Similarly, the body fat determining device 10 is held in such a manner that the thumb of a right hand presses the second measuring electrode 2a and the index finger of the right hand presses the second current path forming electrode 2b.

Next, the subject inputs his (her) weight, height, age, sex and the like by using the keys 3. When the data are completely input, the calculating means calculates a body fat ratio based on the impedance obtained by the impedance measuring means and the data on the subject which are input by means of the keys 3. In this case, various known calculation expressions can be used. The calculation expressions can preliminarily be stored in storing means of the card body 11, for example, a ROM or the like. When the body fat ratio is finally obtained, a result is displayed on the display section 4.

Thus, the body fat determining device 10 according to the present embodiment has the first current path forming electrode 1b provided on just behind the first measuring electrode 1a, and the second current path forming electrode 2b provided on just behind the second measuring electrode 2a.

Accordingly, by a simple operation for holding the body fat determining device 10 in both hands, a current path through both arms and a body can be formed between the index fingers of the hands, and the subject's impedance can be measured on the thumbs of the hands which are positioned in the middle of the current path. In addition, because electrical contact of the fingers with each electrode can surely be performed, positions where fingertips come in contact with the electrodes are constant for each measurement so that a variation in a measured value can be reduced. By performing the natural operation for holding the body fat determining device 10 in both hands to cause the fingertips to come in contact with the electrodes, the body fat ratio can be measured. Thus, the body fat ratio can easily be obtained. In addition, because the body fat determining device 10 can be carried to obtain the body fat ratio at any time, the body fat ratio can be measured without restriction to special places such as a bathroom and the like differently from the body fat determining device according to the prior art. Accordingly, the subject can be caused to be always conscious of body fat. Furthermore, it is also possible to obtain a secondary effect that the subject can learn to always give attention to maintenance of health.

Figure 2:
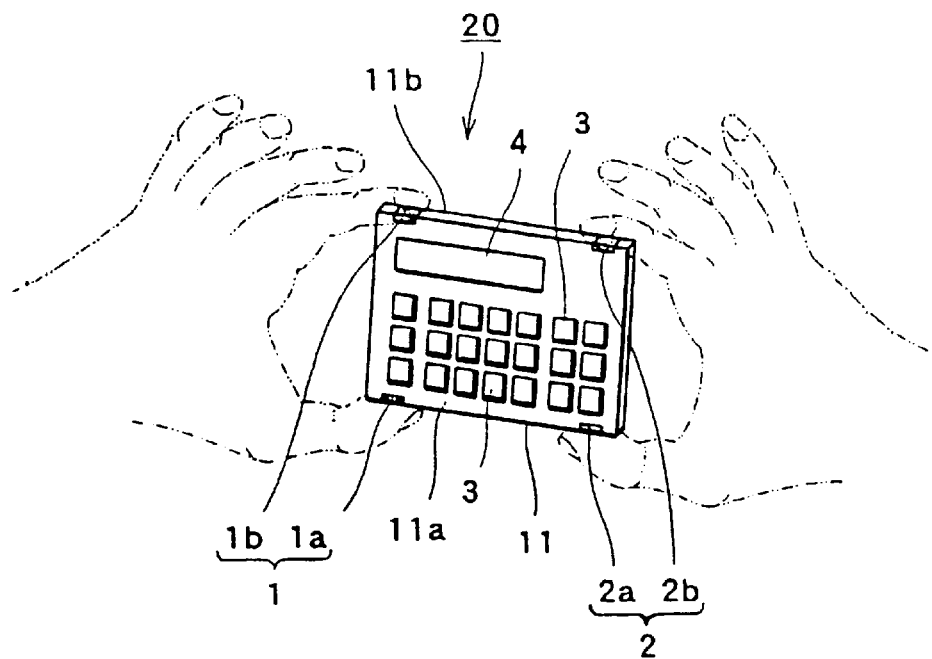
FIG. 2 is a perspective view showing a body fat determining device according to another embodiment of the present invention.

FIG. 2 is a perspective view showing a body fat determining device according to another embodiment of the present invention. A body fat determining device 20 according to the present embodiment is similar to the above-mentioned body fat determining device 10 shown in FIG. 1 except that it has a first electrode pair 1 provided on left sides of upper and lower end faces of a card body 11 and has a second electrode pair 2 provided on right sides of the upper and lower end faces of the card body 11. The same reference numerals as those in FIG. 1 denote corresponding portions. As shown in FIG. 2, the body fat determining device 20 according to the present embodiment has a structure in which the first electrode pair 1 includes a first current path forming electrode 1b provided on the left side of the upper end face of the card body 11 and a first measuring electrode 1a provided on the left side of the lower end face of the card body 11. Similarly, the second electrode pair 2 includes a second current path forming electrode 2b provided on the right side of the upper end face of the card body 11 and a second measuring electrode 2a provided on the right side of the lower end face of the card body 11. With such an arrangement of the electrodes, in a case where the card type body fat determining device 20 is held in both hands, thumbs of the hands are positioned on the first and second measuring electrodes 1a and 2a respectively, and index fingers of the hands are positioned on the first and second current path forming electrodes 1b and 2b respectively.

In the same manner as in the above-mentioned case shown in FIG. 1, a body fat ratio can be measured by using the body fat determining device 20 according to the present embodiment. As shown in a two-dotted chain line in FIG. 2, the body fat determining device 20 is held in such a manner that a subject's thumb and index finger of the left hand press the first measuring electrode 1a and the first current path forming electrode 1b, respectively. Similarly, the body fat determining device 20 is held in such a manner that the subject's thumb and index finger of the right hand press the second measuring electrode 2a and the second current path forming electrode 2b, respectively. Thus, the body fat determining device 20 is held in both hands so that a current path is formed between the index fingers of the hands and an impedance of the subject's body is measured on the thumbs of the hands which are positioned in the middle of the current path.

Next, the subject inputs data on his (her) weight, height, age, sex and the like by using keys 3. Calculating means calculates a body fat ratio based on the impedance obtained by impedance measuring means and the data on the subject which are input by means of the keys 3. When the body fat ratio is finally obtained, a result is displayed on a display section 4.

If the body fat determining device 20 according to the present embodiment is held in both hands, fingertips come in contact with the electrodes so that a body fat ratio can be measured. Consequently, the body fat ratio can be measured very easily. In addition, positions where the fingertips come in contact with the electrodes are constant for each measurement so that a variation in a measured value can be reduced. Furthermore, the body fat ratio can readily be obtained, and the body fat determining device can be carried to determine the body fat ratio. Differently from the body fat determining device according to the prior art, consequently, the body fat ratio can be measured also in places other than special places such as a bathroom and the like.

While the data on the subject have been input after the impedance is measured in the above-mentioned embodiments, the impedance may be measured after the data on the subject are input.

Figure 3:
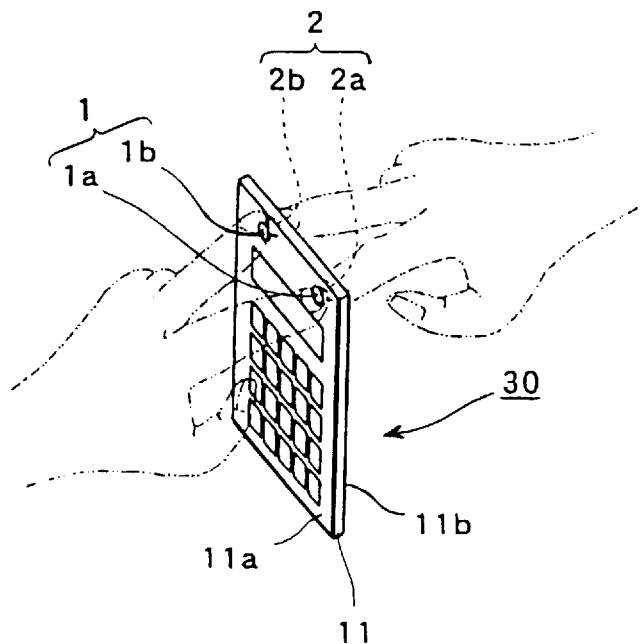
FIG. 3 is a perspective view showing a body fat determining device according to a further embodiment of the present invention.

FIG. 3 shows a body fat determining device according to a further embodiment of the present invention. A body fat determining device 30 shown in FIG. 3 has a first measuring electrode 1a and a first current path forming electrode 1b provided on a surface 11a of a card body 11, and a second measuring electrode 2a and a second current path forming electrode 2b provided on a back face 11b of the card body 11. As shown in a two-dotted chain line in FIG. 3, the body fat determining device according to the present embodiment is held in such a manner that the card body 11 is supported on the surface 11a and the back face 11b with index fingers and middle fingers of both hands, thereby determining a body fat ratio.

Figure 4:
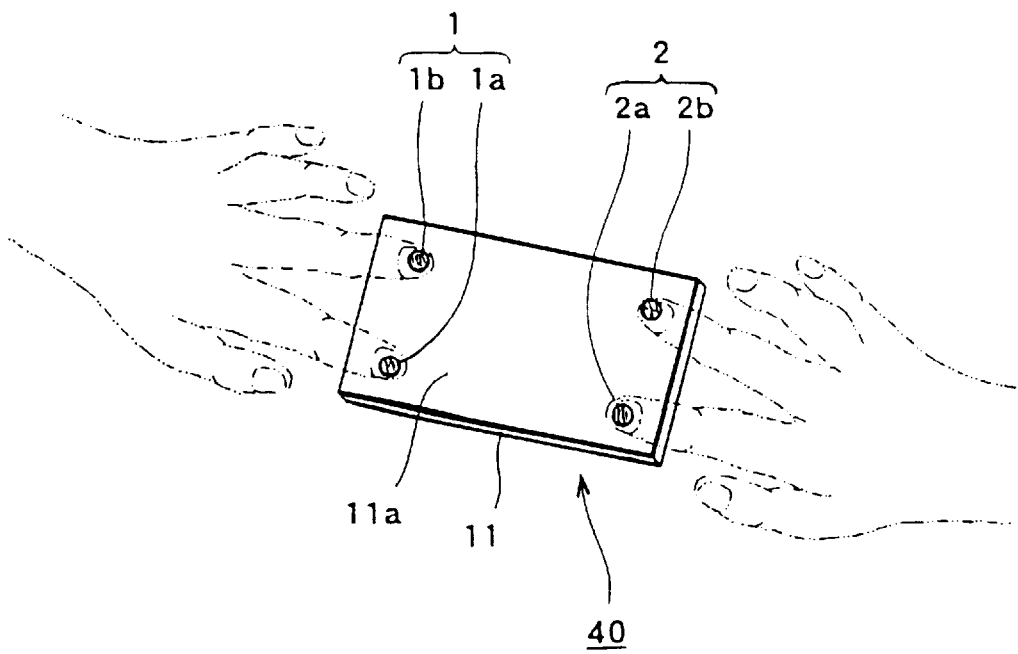
FIG. 4 is a perspective view showing an embodiment in which all electrodes are provided on one of faces of the body fat determining device according to the present invention.

FIG. 4 shows a body fat determining device according to a further embodiment of the present invention in which electrodes are provided on only one of faces of a card body 11. More specifically, all of first and second measuring electrodes 1a and 2a and first and second current path forming electrodes 1b and 2b are provided on a surface 11a of the card body 11. In the present embodiment, the first and second measuring electrodes 1a and 2a are provided in a lower portion of the card body 11, and the first and second current path forming electrodes 1b and 2b are provided in an upper portion of the card body 11.

A body fat determining device 40 according to the present embodiment is put on a table or the like with the electrodes 1a, 1b, 2a and 2b placed on an upper face. In this way, the body fat determining device 40 is used. In the body fat determining device 40 put on the table, an index finger and a middle finger of one of the hands are caused to come in contact with the first measuring electrode 1a and the first current path forming electrode 1b, and an index finger and a middle finger of the other hand are caused to come in contact with the second measuring electrode 2a and the second current path forming electrode 2b respectively as shown in a two-dotted chain line in FIG. 4. Thus, a body fat ratio is measured.

Figure 5:
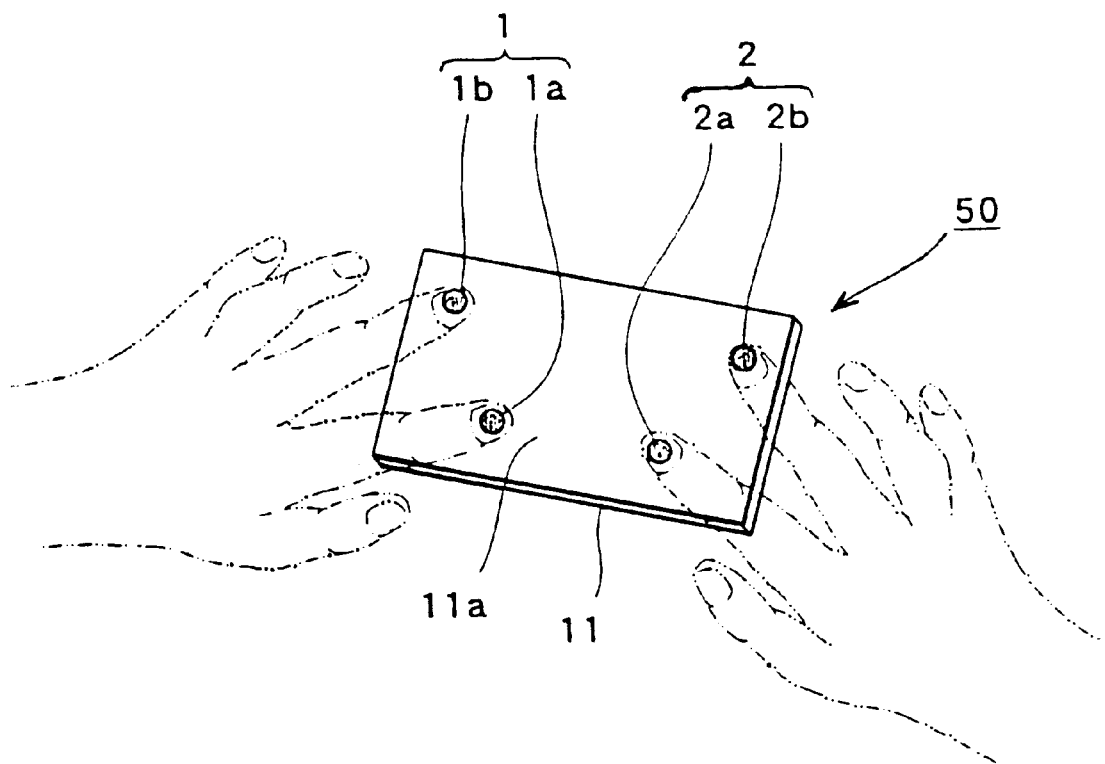
FIG. 5 is a perspective view showing a case where positions of the electrodes according to the embodiment in FIG. 4 are disposed at different position.

In an embodiment shown in FIG. 5, positions of the measuring electrodes 1a and 2a are positioned inward in such a manner that fingers can easily come in contact with the current path forming electrodes 1b and 2b and the measuring electrodes 1a and 2a. A method for using the body fat determining device according to the present embodiment is the same as in the embodiment shown in FIG. 4.

While the case where the function of the body fat determining device is given to the electronic calculator has been described in the embodiments shown in FIGS. 1 to 3, the body fat determining device according to the present invention can be incorporated into various belongings such as a watch, a pedometer, a pager, a portable scale and the like, and can further be constituted as a card having the function of only the body fat determining device as shown in FIGS. 4 and 5.

In the body fat determining device according to the present invention as described above, because the fingertips come in contact with the current path forming electrodes and the measuring electrodes, the positions where the fingertips come in contact with the electrodes are almost constant for each measurement. Accordingly, the formed current path has a constant length. As a result, a variation in a value of the impedance obtained for each measurement is reduced. In the body fat determining device according to the present invention, each measuring electrode is placed in the position on just behind each current path forming electrode. Consequently, by performing the natural operation for holding the body fat determining device in both hands, the fingertips come in contact with the electrodes. Thus, a body fat ratio can easily be measured. In addition, the body fat determining device can be carried to determine the body fat ratio at any time. Differently from the body fat determining device which has been used in special places such as a bathroom and the like, the body fat ratio can be measured in any place. Therefore, the subject can be conscious that attention should be always given to body fat and can further learn to be always careful about maintenance of health.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A body fat determining device comprising:
    a first electrode pair having a first current path forming electrode and a first measuring electrode provided near the first current path forming electrode;
    a second electrode pair having a second current path forming electrode forming a current path with the first current path forming electrode, and a second measuring electrode provided near the second current path forming electrode for measuring an impedance between the first measuring electrode and the second measuring electrode;
    impedance measuring means for measuring the impedance between the first measuring electrode and the second measuring electrode;
    data input means for inputting data on a subject which are necessary for calculation of a body fat ratio; and
    calculating means for calculating the body fat ratio based on the impedance obtained by the impedance measuring means and the data on the subject which are input by the data input means,
    wherein the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes, to form a current path of substantially constant length and to enable the impedance between two points in the middle of the current path to be measured under substantially constant conditions, thereby reducing variations in impedance measurements.

2. The body fat determining device according to claim 1, wherein one of the fingers is a thumb and the other fingers are fingers except the thumb.

3. The body fat determining device according to claim 2, wherein the body fat determining device is of a card type comprising of at least opposite faces, the first current path forming electrode and the second current path forming electrode are provided on one of the faces of the card type body fat determining device, the first measuring electrode and the second measuring electrode are provided on the other face of the card type body fat determining device, the first measuring electrode is provided in a position on just behind the first current path forming electrode, and the second measuring electrode is provided in a position on just behind the second current path forming electrode.

4. The body fat determining device according to claim 2, wherein the body fat determining device is of a card type comprising of at least opposite end faces, the first current path forming electrode and the second current path forming electrode are provided on one of the end faces of the card type body fat determining device, the first measuring electrode and the second measuring electrode are provided on the other end face of the card type body fat determining device, and the first measuring electrode, the first current path forming electrode, the second measuring electrode and the second current path forming electrode are provided in such a manner that the thumbs of both hands are positioned on the first and second measuring electrodes and the fingers other than the thumbs of the hands are positioned on the first and second current path forming electrodes when the card type body fat determining device is held in the hands.

5. The body fat determining device according to claim 1, wherein the body fat determining device is of a card type comprising of at least opposite faces, the first current path forming electrode and the first measuring electrode are provided on one of the faces of the card type body fat determining device, and the second current path forming electrode and the second measuring electrode are provided on the other face of the card type body fat determining device.

6. The body fat determining device according to claim 1, wherein the body fat determining device is of a card type comprising of at least opposite faces, and the first and second current path forming electrodes and the first and second measuring electrodes are provided on one of the faces of the card type body fat determining device.

7. A body fat determining device comprising:
   a first electrode pair having a first current path forming electrode and a first measuring electrode provided near the first current path forming electrode;
   a second electrode pair having a second current path forming electrode forming a current path with the first current path forming electrode, and a second measuring electrode provided near the second current path forming electrode for measuring an impedance between the first measuring electrode and the second measuring electrode;
   impedance measuring means for measuring the impedance between the first measuring electrode and the second measuring electrode;
   data input means for inputting data on a subject which are necessary for calculation of a body fat ratio; and
   calculating means for calculating the body fat ratio based on the impedance obtained by the impedance measuring means and the data on the subject which are input by the data input means,
   wherein the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes when the card type body fat determining device is held in the hands, to form a current path of substantially constant length and to enable the impedance between two points in the middle of the current path to be measured under substantially constant conditions, thereby reducing variations in impedance measurements.

8. The body fat determining device according to claim 6, wherein the fingertip portions of the fingers can electrically come in contact with the first and second current path forming electrodes and the first and second measuring electrodes.

9. The body fat determining device according to claim 7, wherein the fingertip portions of the fingers can electrically come in contact with the first and second current path forming electrodes and the first and second measuring electrodes.

* * * * *

(12) EX PARTE REEXAMINATION CERTIFICATE (5543rd)
United States Patent
Kawanishi et al.

(10) Number: US 6,188,925 C1
(45) Certificate Issued: Oct. 3, 2006

(54) BODY FAT DETERMINING DEVICE

(75) Inventors: Shozo Kawanishi, Nishinomiya (JP);
Masami Yamanaka, Miki (JP);
Yasutoshi Masuda, Akashi (JP)

(73) Assignee: Yamato Scale Co. Ltd., Akashi (JP)

Reexamination Request:
No. 90/006,298, May 21, 2002

Reexamination Certificate for:
Patent No.: 6,188,925
Issued: Feb. 13, 2001
Appl. No.: 09/164,287
Filed: Oct. 1, 1998

(30) Foreign Application Priority Data

Dec. 25, 1997 (JP) ............................................. 9-357510

(51) Int. Cl.
*A61B 5/053* (2006.01)
*G01N 27/02* (2006.01)
*G01N 33/483* (2006.01)

(52) U.S. Cl. ........................ 600/547; 345/173; 345/174
(58) Field of Classification Search ................. 600/300,
600/372, 382, 393, 547, 554; 128/897; 345/173,
345/174; 702/19, 57
See application file for complete search history.

(56) References Cited

U.S. PATENT DOCUMENTS 4,949,727 A * 8/1990 Yamazaki et al. .......... 600/547
5,579,782 A * 12/1996 Masuo ........................ 600/547
6,243,651 B1 * 6/2001 Masuo ......................... 702/19

FOREIGN PATENT DOCUMENTS

JP 05-337096 * 12/1993 ................. 600/547
WO WO 97/01303 * 1/1997

* cited by examiner

*Primary Examiner*—David O. Reip

(57) ABSTRACT

Provided is a small-sized body fat determining device capable of easily determining a body fat ratio. A first electrode pair (1) and a second electrode pair (2) are provided on upper left and right sides of a surface (11a) and a back face (11b) of a card body (11) of a card type electronic calculator, respectively. The first electrode pair (1) includes a first measuring electrode (1a) provided on the surface (11a) of the card body (11), and a first current path forming electrode (1b) provided on the back face (11b) of the card body (11). The second electrode pair (2) includes a second measuring electrode (2a) provided on the surface (11a) of the card body (11), and a second current path forming eletrode (2b) provided on the back face (11b) of the card body (11). An impedance between the first measuring electrode (1a) and the second measuring electrode (2a) is measured by impedance measuring means provided in the card body (11).

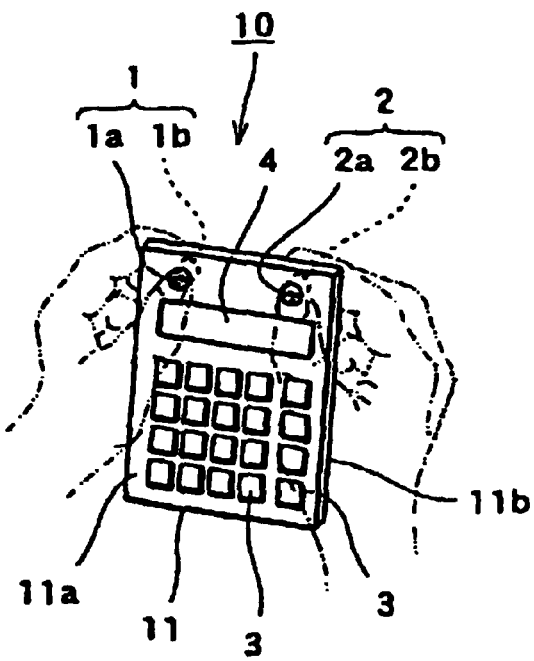

US 6,188,925 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 6 and 8 is confirmed.

Claims 3–5 and 7 are determined to be patentable as amended.

Claim 9, dependent on an amended claim, is determined to be patentable.

3. [The] *A* body fat determining device [according to claim 2,] *comprising:*
  *a first electrode pair having a first current path forming electrode and a first measuring electrode provided near the first current path forming electrode;*
  *a second electrode pair having a second current path forming electrode forming a current path with the first current path forming electrode, and a second measuring electrode provided near the second current path forming electrode for measuring an impedance between the first measuring electrode and the second measuring electrode;*
  *impedance measuring means for measuring the impedance between and first measuring electrode and the second measuring electrode;*
  *data input means for inputting data on a subject which are necessary for calculation of a body fat ratio;*
  *calculating means for calculating the body fat ratio based on the impedance obtained by the impedance measuring means and the data on the subject which are input by the data input means;*
  *wherein the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes, to form a current path of substantially constant length and to enable the impedance between two points in the middle of the current path to be measured under substantially constant conditions, thereby reducing variations in impedance measurements;*
  *wherein one of the fingers is a thumb and the other fingers are fingers except the thumb; and*
  wherein the body fat determining device is of a card type comprising of at least opposite faces, the first current path forming electrode and the second current path forming electrode are provided on one of the faces of the card type body fat determining device, the first measuring electrode and the second measuring electrode are provided on the other face of the card type body fat determining device, the first measuring electrode is provided in a position on just behind the first current path forming electrode, and the second measuring electrode is provided in a position on just behind the second current path forming electrode.

4. [The] *A* body fat determining device [according to claim 2,] *comprising:*
  *a first electrode pair having a first current path forming electrode and a first measuring electrode provided near the first current path forming electrode;*
  *a second electrode pair having a second current path forming electrode forming a current path with the first current path forming electrode, and a second measuring electrode provided near the second current path forming electrode for measuring an impedance between the first measuring electrode and the second measuring electrode;*
  *impedance measuring means for measuring the impedance between the first measuring electrode and the second measuring electrode;*
  *data input means for inputting data on a subject which are necessary for calculation of a body fat ratio;*
  *calculating means for calculating the body fat ratio based on the impedance obtained by the impedance measuring means and the data on the subject which are input by the data input means;*
  *wherein the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes, to form a current path of substantially constant length and to enable the impedance between two points in the middle of the current path to be measured under substantially constant conditions, thereby reducing variations in impedance measurements;*
  *wherein one of the fingers is a thumb and the other fingers are fingers except the thumb; and*
  *wherein the body fat determining device is of a card type comprising of at least opposite end faces, the first current path forming electrode and the second current path forming electrode are provided on one of the end faces of the card type body fat determining device, the first measuring electrode and the second measuring electrode are provided on the other end face of the card type body fat determining device, and the first measuring electrode, the first current path forming electrode, the second measuring electrode and the second current path forming electrode are provided in such a manner that the thumbs of both hands are positioned on the first and second measuring electrodes and the fingers other than the thumbs of the hands are positioned on the first and second current path forming electrodes when the card type body fat determining device is held in the hands.*

5. [The] *A* body fat determining device [according to claim 2,] *comprising:*
  *a first electrode pair having a first current path forming electrode and a first measuring electrode provided near the first current path forming electrode;* a second electrode pair having a second current path forming electrode forming a current path with the first current path forming electrode, and a second measuring electrode provided near the second current path forming electrode for measuring an impedance between the first measuring electrode and the second measuring electrode;

impedance measuring means for measuring the impedance between the first measuring electrode and the second measuring electrode;

data input means for inputting data on a subject which are necessary for calculation of a body fat ratio;

calculating means for calculating the body fat ratio based on the impedance obtained by the impedance measuring means and the data on the subject which are input by the data input means;

wherein the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes, to form a current path of substantially constant length and to enable the impedance between two points in the middle of the current path to be measured under substantially constant conditions, thereby reducing variations in impedance measurements; and wherein the body fat determining device is of a card type comprising of at least opposite faces, the first current path forming electrode and the first measuring electrode are provided on the of the faces of the card type body fat determining device, and the second current path forming electrode and the second measuring electrode are provided on the other face of the card type body fat determining device.

7. A body fat determining device comprising:

a first electrode pair having a first current path forming electrode and a first measuring electrode provided near the first current path forming electrode;

a second electrode pair having a second current path forming electrode forming a current path with the first current path forming electrode, and a second measuring electrode provided near the second current path forming electrode for measuring an impedance between the first measuring electrode and the second measuring electrode;

impedance measuring means for measuring the impedance between the first measuring electrode and the second measuring electrode;

data input means for inputting data on a subject which are necessary for calculation of a body fat ratio; and calculating means for calculating the body fat ratio based on the impedance obtained by the impedance measuring means and the data on the subject which are input by the data input means, wherein *the body fat determining device is of a card type,* the first and second current path forming electrodes and the first and second measuring electrodes are sized and provided in positions where one of the fingers of each of the subject's hands can electrically come in contact with each of the first and second measuring electrodes and one of the other fingers of each of the subject's hands can electrically come in contact with each of the first and second current path forming electrodes when the card type body fat determining device is held in the hands, to form a current path of substantially constant length and to enable the impedance between two points in the middle of the current path to be measured under substantially constant conditions, thereby reducing variations in impedance measurements.

* * * * *